United States Patent [19]

Yoshioka et al.

[11] Patent Number: 5,116,608
[45] Date of Patent: May 26, 1992

[54] PERMANENT WAVING COMPOSITION

[75] Inventors: Issei Yoshioka, Osaka; Yoichi Kamimura, Nara; Masao Kitano, Kamakura; Yujiro Goto, Kawasaki, all of Japan

[73] Assignee: Seiwa Kasei Co., Ltd., Osaka, Japan

[21] Appl. No.: 411,979

[22] Filed: Sep. 25, 1989

[30] Foreign Application Priority Data

Sep. 29, 1988 [JP] Japan .................. 63-245795

[51] Int. Cl.$^5$ .................................................. A61K 7/09
[52] U.S. Cl. ............................................ 424/72; 424/71
[58] Field of Search ...................................... 424/72, 71

[56] References Cited

U.S. PATENT DOCUMENTS

| | | | |
|---|---|---|---|
| 2,540,494 | 2/1951 | Schwarz | 424/72 X |
| 3,093,146 | 6/1963 | Kalopissis et al. | 132/203 |
| 4,973,475 | 11/1990 | Schnetzinger | 424/71 X |

FOREIGN PATENT DOCUMENTS

| | | | |
|---|---|---|---|
| 61-069716 | 4/1986 | Japan | 424/72 |
| 62-205014 | 9/1987 | Japan | . |
| 589956 | 5/1953 | United Kingdom | 424/72 |
| WO 88/02997 | 5/1988 | World Int. Prop. O. | . |

OTHER PUBLICATIONS

Patent Abstracts of Japan, vol. 10, No. 112 (C-342) (2169), Apr. 25, 1986, (JP 60-243,011).
Patent Abstracts of Japan, vol. 6, No. 139 (C-116) (1017), Jul. 28, 1982, (JP 57-62217).

*Primary Examiner*—Thurman K. Page
*Assistant Examiner*—D. Colucci
*Attorney, Agent, or Firm*—Armstrong & Kubovcik

[57] ABSTRACT

An aqueous permanent waving composition containing as a reducing agent a quaternary ammoniomercaptan or its salt of the formula:

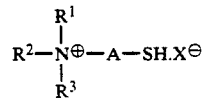

wherein $R^1$, $R^2$, and $R^3$ are an alkyl group or a hydroxyalkyl group, A is an alkylene group, and X is a halogen atom, $NO_3$, $\frac{1}{2}SO_4$, OH or $R^4OSO_3$ in which $R^4$ is an alkyl group, which can be used under an acidic, neutral or alkaline condition and can impart good waves to hairs with a little damage of the hairs and a little foul smell.

4 Claims, No Drawings

PERMANENT WAVING COMPOSITION

BACKGROUND OF THE INVENTION

The present invention relates to a composition for permanently waving hair, applied in the first stage of permanent wave treatment of the hair, and more particularly to a permanent waving composition which has a reduced foul smell and is less damaging to the hair and moreover which can provide good wave to the hair.

Reducing and oxidizing agents have been generally used in the permament waving treatment of hairs such as human and animal hairs. The hair is put under stress, for example, by winding the hair on rods or rollers, and a waving lotion containing a reducing agent is applied to the wound or curled hair, whereby disulfide linkages of cystine included in keratin protein of the hair are cleaved to produce mercapto groups by means of the reducing agent. The waving lotion is an aqueous solution containing as a main component a reducing agent, e.g. mercaptans (namely thiols) such as thioglycolic acid and cysteine, to which a basic material such as ammonia, monoethanolamine or triethanolamine is usually added to adjust to pH 9.0 to 9.5. An aqueous solution of an oxidizing agent such as sodium bromate or hydrogen peroxide is then applied to the curled hair, thereby oxidizing the mercapto groups to form new disulfide linkages. Thus the permanent wave is formed.

Thioglycolic acid which has been widely used in practice as the reducing agent of the waving lotion, has a strong foul smell. Accordingly, the use of thioglycolic acid has a problem that not only the waving lotion itself has a uncomfortable smell, but also the smell remains on the hair even after the wavetreatment. Moreover, since thioglycolic acid and cysteine exhibit the reducing action only in an alkaline region, waving lotions using these reducing agents are kept alkaline. They have a problem that the hair is damaged and gives a feeling of being dry, since the hair is swollen by an alkali, so that a part of keratin protein is eluted and the remaining part of the hair undergoes physical and chemical changes.

It is an object of the present invention to provide a permanent waving composition which has no foul smell and does not cause any substantial damage of hairs.

A further object of the invention is to provide a permanent waving composition which can be used under a neutral or acidic condition.

These and other objects of the present invention will become apparent from the description hereinafter.

SUMMARY OF THE INVENTION

It has now been found that a permanent waving composition which has little foul smell, and which can be used for permanent wave treatment of the hair under a neutral or acidic condition, so the damage of the hair is remarkably decreased, and moreover which can provide good wave to the hair, is obtained by using a specified quaternary ammoniomercaptan or its salt as a reducing agent.

In accordance with the present invention, there is provided a permanent waving composition comprising 0.5 to 10% by weight of a quaternary ammoniomercaptan or its salt of the formula (1):

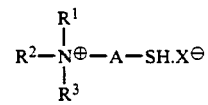

wherein $R^1$, $R^2$ and $R^3$ are the same or different and each is an alkyl group having 1 to 3 carbon atoms or a hydroxyalkyl group having 1 to 3 carbon atoms, A is ethylene, propylene or isopropylene, and X is Cl, Br, I, $NO_3$, $\frac{1}{2}SO_4$, OH or $R^4OSO_3$ in which $R^4$ is an alkyl group having 1 to 3 carbon atoms.

The quaternary ammoniomercaptan or its salt represented by the formula (1) has an —SH group, but it merely gives out a very weak foul smell because it is nonvolatile. Accordingly, the permanent waving composition of the invention containing the quaternary ammoniomercaptan or its salt (1) as a reducing agent has little or a little foul smell, and it scarcely gives out the smell during the hair treatment, to say nothing of after treatment. Furthermore, since the compounds of the formula (1) have a high water solubility and are basic, they have a high affinity for the hair which has the isoelectric point in the vicinity of pH 4, and are easy to permeate into the hair. The compounds (1) also have the advantage that dimers in the oxidized form by-produced from the compounds (1) by oxidation treatment are low in molecular weight and soluble in water and, therefore, they can be easily rinsed out and do not remain on the hair. Further, since the compounds (1) are basic, and accordingly since they have a high affinity for the hair even under an acidic condition and can exhibit the reducing action even in a neutral or acidic region, permanent waving treatment of the hair can be conducted in a neutral or acidic region, whereby damage of the hair due to an alkali is prevented. Moreover, the effect of imparting wave to the hair is superior to conventional permanent waving compositions of thioglycolic acid type and of cysteine type.

DETAILED DESCRIPTION

Representative examples of the quaternary ammoniomercaptan or its salt represented by the above formula (1) are, for instance, 2-trimethylammonioethanethiol, 2-trimethylammonioethanethiol chloride, 2-trimethylammonioethanethiol bromide, 2-trimethylammonioethanethiol iodide, 2-trimethylammonioethanethiol nitrate, 2-trimethylammonioethanethiol sulfate, 2-trimethylammonioethanethiol methylsulfate, 2-triethylammonioethanethiol, chloride, 2-triethylammonioethanethiol, 2-triethanolammonioethanethiol chloride, 2-tripropylammonioethanethiol, 2-tripropylammonioethanethiol chloride, 2-triisopropylammonioethanethiol, 2-tris(2-hydroxypropyl)ammonioethanethiol, 2-tris(2-hydroxypropyl)ammonioethanethiol chloride, 3-trimethylammoniopropanethiol, 3-trimethylammoniopropanethiol chloride, 2-trimethylammoniopropanethiol, 2-trimethylammoniopropanethiol chloride, and the like.

The permanent waving composition of the present invention is prepared, for instance, as follows: Basically, the composition of the invention is prepared in a conventional manner by using as the reducing agent the compound (1) instead of conventionally used reducing agents such as thioglycolic acid and cysteine. The compound (1) is added to water with common additives conventionally used for the preparation of permanent waving compositions. The additives include, for instance, a carbonate such as ammonium carbonate or ammonium bicarbonate, anionic, cationic, non-ionic and amphoteric surface active agents, an emulsifier, a penetrating agent, a hair tonic agent, a chelating agent, a coloring agent, a perfume, and the like.

The composition of the present invention may or may not contain an alkaline substance which is conventionally used for alkalinizing a permanent waving composition, e.g. ammonia, monoethanolamine, diethanolamine, triethanolamine, 2-amino-2-methylpropane, 2-amino-2-methyl-1,3-propanediol, sodium hydroxide or potassium hydroxide. Since the compound (1) can exhibit the reducing action even in a neutral or acidic region, namely in a pH region of about 8 to about 4, the waving composition of the invention does not always require to contain the alkalinizing agent, whereas conventional waving compositions must contain the alkalinizing agent.

The content of the compound (1) in the waving composition is from 0.5 to 10 % by weight. When the amount of the compound (1) is less than 0.5% by weight, the reducing action is not sufficiently exhibited and disulfide linkages in the hair are not sufficiently broken, so satisfactory permanent wave cannot be provided to the hair. The use of the compound (1) in an amount of more than 10% by weight should be avoided, since the hair is waved too strong.

A conventionally used reducing agent may be used in combination with the compound (1) in an amount such that the effects produced by the compound (1) are not substantially impaired. Representative examples of such a reducing agent are, for instance, thioglycolic acid and its salt such as ammonium thioglycolate or thioglycolic acid monoethanolamine, other thioglycolic acid derivatives such as thioglycolic acid amide, thioglycolic acid hydrazide or glyceryl monothioglycolate, cysteine and the salts thereof such as L-cysteine, L-cysteine hydrochloride, DL-cysteine or DL-cysteine hydrochloride, homocysteine and the salts thereof, thiomalic acid and the salts thereof, thiolactic acid and the salts thereof, cysteamine and the salts thereof, thioglycerin, and the like.

In particular, in the present invention, it is preferable to add peptide or its derivatives to the permanent waving composition. The addition of peptide or its derivatives is effective in that the damage of hair owing to wave treatment is further prevented. When the composition of the invention is applied to the hair, the compound (1) penetrates into the hair and splits the disulfide linkages (S—S linkages) of cystine to produce mercapto groups (—SH). At that time, peptide or its derivative penetrates into the inside of the hair, thus is absorbed by the hair tissues. Peptide or its derivative has a similar peptide linkage to keratin which is a protein constituting the hair. Accordingly, linkages are produced between the absorbed peptide or its derivative and the hair tissues, for example, by ionic bonds between the side chain of an acidic amino acid such as glutamic acid or aspartic acid and the side chain of a basic amino acid such as arginine, lysine or histidine that both the absorbed peptide compound and keratin have, or by hydrogen bonds between the peptide chains, or by van der Waals force between the side chains of a hydrophobic amino acid. Since the absorbed peptide compound is firmly fixed to the hair, it is not easily rinsed off even if the hair is washed with water. Thus, the hair is reinforced by the peptide or its derivative absorbed, so the damage of the hair owing to the permanent waving treatment is decreased or prevented.

The peptide as mentioned above is obtained by hydrolyzing natural proteins with an acid, an alkali or an enzyme, e.g. proteins such as gelatin which is collagen or its denatured product, keratin, silk, casein, elastin, conchyolin, soybean protein, egg albumen and egg yolk; and composite proteins containing glycose, phosphoric acid and fat.

Representative examples of the acid used in the acid hydrolysis of proteins are inorganic acids such as hydrogen chloride, sulfuric acid, phosphoric acid and hydrobromic acid, and organic acids such as acetic acid and formic acid.

Representative examples of the alkali used in the alkali hydrolysis of proteins are inorganic alkaline substances such as lithium hydroxide, sodium hydroxide, potassium hydroxide, barium hydroxide, sodium carbonate, potassium carbonate and lithium carbonate.

Representative examples of the enzyme used in the enzymatic hydrolysis of proteins are acidic proteolytic enzymes such as pepsin, proctase A and proctase B, and neutral proteolytic enzymes such as papain, bromelyn, thermolysin, trypsin, pronase and chymotrypsin. Neutral proteolytic enzymes produced by microorganisms, e.g. subtilisin and Staphylococcus protease, can also be used. The enzymes may be used in any forms, for example, in the form of cells containing enzymes, and membranes or particles wherein an enzyme or enzyme-containing cells are immobilized.

The acid, alkali or enzyme hydrolysis of proteins to produce the peptide is described in detail, for example, in Japanese Unexamined Patent Publication Kokai No. 61-69717 and No. 63-105000.

Peptides having an average molecular weight of 150 to 5,000 are preferably used in the present invention. Upon the hydrolysis of proteins, the hydrolysis conditions are suitably selected to produce such peptides.

When the peptides are represented by the formula (2)

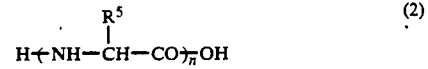

the average molecular weight of 150 to 5,000 corresponds to n=2 to 30. In the formula (2), $R^5$ represents the side chain of an amino acid constituting the peptide. The peptide-constituting amino acid having such a side chain $R^5$ includes, for instance, alanine, glycine, valine, leucine, isoleucine, proline, phenylalanine, tyrosine, serine, threonine, methionine, arginine, histidine, lysine, aspartic acid, asparagine, glutamic acid, glutamine, cystine, cysteic acid, tryptophan, hydroxyproline, and hydroxylysine.

The derivatives of the peptides include, for instance, acylated peptides and their salts, quaternary ammonium derivatives of peptides, and esters of peptides.

Representative acylated peptides and their salts are compounds of the formula (3):

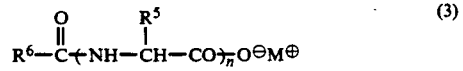

wherein $R^5$ is a side chain of the peptide-constituting amino acid, $R^6$ is a long chain alkyl group having 8 to 20 carbon atoms or a long chain alkenyl group having 8 to 20 carbon atoms, n is an integer of 2 to 30, and M is hydrogen, an alkali metal such as sodium or potassium, ammonium, or an onium of an organic alkanolamine such as monoethanolamine, diethanolamine or 2-amino-2-methyl-1,3propanediol. The acylated peptides and their derivatives are provided with a surface active ability by acylation in addition to the characteristics of the peptides and, therefore, they accelerate the penetration of the quaternary ammoniomercaptan or its salt represented by the formula (1) and also have a more increased action of wetting the hair and imparting a luster to the hair.

Representative quaternary ammonium derivatives of the peptides are compounds of the formula (4):

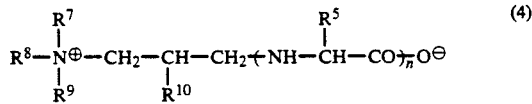

wherein $R^5$ is as defined above, $R^7$, $R^8$ and $R^9$ are independently an alkyl group having 1 to 20 carbon atoms, or one or two of $R^7$ to $R^9$ are an alkyl group having 1 to 20 carbon atoms and the residue is a hydroxyalkyl group having 1 to 3 carbon atoms or benzyl group, and $R^{10}$ is hydrogen or hydroxyl group. The quaternary ammonium derivatives have a further improved property of being adsorbed by the hair because the peptides are converted into a quaternary structure, and accordingly they exhibit the above-mentioned actions of the peptides more noticeably.

Representative peptide esters are compounds of the formula (5):

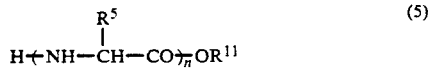

wherein $R^5$ and n are as defined above, and $R^{11}$ is a straight or branched alkyl group having 1 to 18 carbon atoms or a straight or branched hydroxyalkyl group having 1 to 18 carbon atoms. The peptide esters have improved action of imparting wettability, oily feeling and luster to the hair because of introduction of a higher alkyl or hydroxyalkyl group to the peptides by esterification, and accordingly they give a better finish to the hair in cooperation with the characteristics of the peptides.

In addition to the quaternary ammoniomercaptan compounds (1) and the peptides or their derivatives, the permanent waving composition of the present invention may be suitably incorporated with usual additives as mentioned before.

Examples of anionic surface active agents are, for instance, an alkyl sulfate such as ammonium lauryl sulfate, lauryl sulfate ethanolamine, sodium lauryl sulfate or lauryl sulfate triethanolamine; a polyoxyethylene alkylether sulfate such as polyoxyethylene(2) lauryl ether sulfate triethanolamine or a sodium polyoxyethylene(3) alkyl ether sulfate wherein the alkyl group is one having 11 to 15 carbon atoms or a mixture thereof; an alkylbenzene sulfonate such as sodium laurylbenzene sulfonate or laurylbenzene sulfonate triethanolamine; a polyoxyethylene alkyl ether acetate such as sodium polyoxyethylene(3) tridecyl ether acetate; an N-acylamino acid salt such as sodium salt of coconut oil fatty acid sarcosine, lauroyl sarcosine triethanolamine, sodium salt of lauroylmethyl-$\beta$-alanine, sodium lauroyl-L-glutamate, lauroyl-L-glutamic acid triethanolamine, sodium coconut oil fatty acid-L-glutamate, coconut oil fatty acid-L-glutamic acid triethanolamine, sodium coconut oil fatty acid methyl taurate or sodium lauroyl methyl taurate; and other anionic surface active agents such as a sodium isethionate, sodium hardened coconut oil fatty acid glycerol sulfate, undecylenoylamidoethyl disodium sulfosuccinate, sodium octylphenoxydiethoxyethyl sulfonate, oleinamide disodium sulfosuccinate, dioctyl sodium sulfosuccinate, lauryl disodium sulfosuccinate, a polyoxyethylene(8 to 10) alkyl ether phosphate (alkyl group having 12 to 15 carbon atoms), sodium polyoxyethylene oleyl ether phosphate, sodium polyoxyethylene cetyl ether phosphate, lauryl disodium polyoxyethylenesulfosuccinate, sodium polyoxyethylene lauryl ether phosphate, sodium lauryl sulfoacetate, and sodium tetradecenesulfonate.

Examples of cationic surface active agents are, for instance, distearyldimethylammonium chloride, dipolyoxyethyleneoleylmethylammonium chloride, stearyldimethylbenzylammonium chloride, stearyltrimethylammonium chloride, cetyltrimethylammonium chloride, tri(polyoxyethylene)stearylammonium chloride, polyoxypropylenemethyldiethylammonium chloride, myristyldimethylbenzylammonium chloride, and lauryltrimethylammonium chloride.

Examples of amphoteric surface active agents are, for instance, a 2-alkyl-N-carboxymethyl-N-hydroxyethylimidazolium betaine, sodium undecylhydroxyethylimidazolium betaine, undecyl-N-hydroxyethyl-N-carboxymethylimidazolium betaine, stearyldihydroxyethyl betaine, stearyldimethylaminoacetic acid betaine, coconut oil alkyl betaine, coconut oil fatty acid amide propyl betaine, coconut oil alkyl N-carboxyethyl-N-hydroxyethylimidazolium betaine sodium salt, coconut oil alkyl N-carboxyethoxyethyl-N-carboxyethylimidazolium disodium hydroxide, coconut oil alkyl N-carboxymethoxyethyl-N-carboxymethylimidazolium disodium lauryl sulfate, and N-coconut oil fatty acid acyl L-arginineethyl.DL-pyrrolidone carboxylic acid salt.

Examples of non-ionic surface active agents are, for instance, polyoxyethylene(7) $C_{12\text{-}14}$ alkyl ether, polyoxyethylene octylphenyl ether, polyoxyethylene oleyl ether, polyoxyethylene glycerine oleate, polyoxyethylene stearyl ether, polyoxyethylene cetyl ether, polyoxyethylene cetylstearyl ether, polyoxyethylene(40) sorbitol lanolin, polyoxyethylene nonylphenyl ether, polyoxyethylene polyoxypropylene cetyl ether, polyoxyethylene polyoxypropylene decyltetradecyl ether, polyoxyethylene lanolin, polyoxyethylene lanolin alcohol, and polyoxypropylene stearyl ether.

Examples of synthetic polymers used as an additive are, for instance, a cationic polymer such as cationized cellulose, cationized hydroxyethyl cellulose, poly(diallyldimethylammonium chloride), polyvinylpyridine or polyethyleneimine, an amphoteric polymer, and an anionic polymer.

Examples of thickeners are, for instance, isostearic acid diethanolamide, undecylenic acid monoethanolamide, oleic acid diethanolamide, tallow fatty acid monoethanolamide, hardened tallow fatty acid diethanolamide, stearic acid diethanolamide, stearic acid diethylaminoethylamide, stearic acid monoethanolamide, myristic acid diethanolamide, coconut oil fatty acid ethanolamide, coconut oil fatty acid diethanolamide, lauric acid isopropanolamide, lauric acid ethanolamide, lauric acid diethanolamide, and lanolin fatty acid diethanolamide.

Examples of wetting agents are, for instance, extracts from animals and plants, polysaccharides or their derivatives, propylene glycol, 1,3-butylene glycol, ethylene glycol, glycerin, and polyethylene glycol.

Examples of a lower alcohol used as an additive are, for instance, ethanol, methanol, propanol, and isopropanol.

Examples of an amino acid used as an additive are, for instance, L-aspartic acid, sodium L-aspartate, DL-alanine, L-arginine, glycine, L-glutamic acid, L-cysteine, and L-threonine.

In addition to the above additives, the composition of the present invention may also contain other known additives such as a pH adjusting agent, a perfume, an antiseptic agent, a chelating agent such as EDTA or its salts, a colorant, a hair tonic agent, and the like, as mentioned before.

The quaternary ammoniomercaptan compounds (1) used as the reducing agent in the permanent waving composition of the present invention have the feature that they exhibit their reduction action even under a neutral or acidic condition, and they of course exhibit the reduction action under an alkaline condition. Therefore, the permanent waving composition can be prepared in a pH region as wide as from 4.5 to 10. When the pH of the composition is adjusted to an alkaline region, the compounds (1) indicate a stronger reducing action and, therefore, they exhibit a strong wave-imparting action of such an extent as cannot be achieved by conventional waving lotions using thioglycolic acid or cysteine reducing agents. Therefore, it is possible to prepare a permanent waving composition capable of providing a strong wave to the hair by adjusting the composition to an alkaline region and incorporating a peptide or its derivative into the composition in order to prevent damage of the hair owing to waving treatment.

As a neutralizing lotion used for oxidation after the application of the permanent waving lotion of the invention, conventional neutralizing lotions can be used in the present invention, e.g. a neutralizing lotion containing a bromic acid salt such as sodium bromate or potassium bromate, and a neutralizing lotion containing hydrogen peroxide.

The present invention is more specifically described and explained by means of the following Examples, in which all % and parts are by weight unless otherwise noted.

EXAMPLE 1

A permanent waving lotion having the composition shown in Table 1 was prepared by using 2-trimethylammonioethanethiol chloride as the reducing agent. After dissolving the ingredients in water, the waving lotion was adjusted with aqueous ammonia to pH 6.8 falling in a neutral region.

COMPARATIVE EXAMPLE 1

A permanent waving lotion having the composition shown in Table 1 was prepared by using a 50% aqueous solution of ammonium thioglycolate. For comparison with the waving lotion of Example 1, the waving lotion was adjusted to pH 6.8.

COMPARATIVE EXAMPLE 2

The procedure of Comparative Example 1 was repeated except that the pH of the waving lotion was adjusted to 9.2 falling in an alkaline region.

TABLE 1

| Ingredients (part) | Example 1 | Comparative Example 1 | Comparative Example 2 |
| --- | --- | --- | --- |
| 2-Trimethylammonioethanethiol chloride | 6.0 | — | — |
| Ammonium thioglycolate (50% aqueous soln.) | — | 12.0 | 12.0 |
| Ammonium bicarbonate | 2.5 | 2.5 | — |
| Monoethanolamine | — | — | 1.0 |
| Polyoxyethylene nonylphenyl ether | 0.2 | 0.2 | 0.2 |
| EDTA | 0.1 | 0.1 | 0.1 |
| Aqueous ammonia (28%) | *1 | *1 | *2 |
| Purified water | residue | residue | residue |
| Total | 100 | 100 | 100 |

(Notes)
*1 Aqueous ammonia was used in an amount to adjust to pH 6.8.
*2 Aqueous ammonia was used in an amount to adjust to pH 9.2.

Using the permanent waving lotions obtained in Example 1 and Comparative Examples 1 and 2, the following tests (Test Nos. 1 to 4) were made, wherein a 6% aqueous solution of sodium bromate was used for oxidization treatment.

TEST 1

(1) Preparation of Samples

A bundle of 10 woman's hairs (length about 18 cm) untreated by permanent waving and dyeing was washed with a 2% aqueous solution of polyoxyethylene nonylphenyl ether, air-dried at room temperature and subjected to the tests.

(2) Testing

The hair bundles were wound on plastic rods having a diameter of 1 cm. Each of the permanent waving lotions obtained in Example 1 and Comparative Examples 1 and 2 was sufficiently applied to each of the wound hair bundles, and allowed to stand for 15 minutes at room temperature. After washing with water, a 6% aqueous solution of sodium bromate was applied to the hair bundles and allowed to stand for 10 minutes at room temperature. The hair bundles were unfastened from the rods, washed with water and air-dried at room temperature. The thus treated hair bundles were hung down, and the diameter of curl was measured.

The curled hair bundles were then washed 5 times with a 2% aqueous solution of polyoxyethylene nonylphenyl ether at intervals of 24 hours with lightly straightening the hair bundle by hand, and the diameter of curl was measured.

The results are shown in Table 2.

TABLE 2

| Sample | Diameter of curl (mm) Number of washings | | | | | |
|---|---|---|---|---|---|---|
| | 0 | 1 | 2 | 3 | 4 | 5 |
| Example 1 | 23.6 | 25.7 | 32.6 | 40.5 | 43.0 | 44.1 |
| Com. Ex. 1 | 25.2 | 29.0 | 35.9 | 43.8 | 48.6 | 51.1 |
| Com. Ex. 2 | 23.8 | 26.0 | 32.9 | 41.3 | 44.2 | 45.2 |

As shown in Table 2, the cold waving lotion of Example 1 according to the present invention could provide the hair with a strong wave having a small curl diameter and a good curl retainability, as compared with the waving lotion of Comparative Example 1 prepared using ammonium thioglycolate as the reducing agent and adjusted to the same pH 6.8 as the waving lotion of Example 1. Also, as compared with the waving lotion of Comparative Example 2 prepared using ammonium thioglycolate as the reducing agent and adjusted to an alkaline region, namely pH 9.2, the curl diameter of the hair treated with the waving lotion of Example 1 is smaller and the waving lotion of Example 1 had a better wave-imparting effect.

TEST 2

The hair bundles treated in Test 1 were used as samples, and the curl retainability was estimated.

The results are shown in Table 3.

The curl retention of the curled hair bundles was measured as follows:

The curled hair bundle was washed with water, wound on a roller having a diameter of 20 mm and fastened. After air drying, the hair bundle was unfastened from the roller, hung down and allowed to stand in a room to observe the change in curl retention with the lapse of time.

The curl retention percentage was calculated according to the following equation.

$$\text{Curl retention (\%)} = \frac{L - Lt}{L - Lo} \times 100$$

L: Length of the hair bundle straightened (L=18 cm)
Lo: Distance between both ends of the curled hair bundle when unfastened from the roller
Lt: Distance between both ends of the curled hair bundle after hung down for a prescribed period of time

TABLE 3

| Sample | Change in curl retention with the lapse of time | | |
|---|---|---|---|
| | After 1 day | After 5 days | After 10 days |
| Example 1 | 88% | 85% | 81% |
| Com. Ex. 1 | 83% | 77% | 71% |
| Com. Ex. 2 | 86% | 82% | 78% |

It is observed in Table 3 that the waving lotion of Example 1 shows a larger curl retention than the waving lotion of Comparative Example 2 adjusted to an alkaline pH region, namely pH 9.2, to say nothing of the waving lotion of Comparative Example 1 adjusted to a neutral pH region, namely pH 6.8. From these results, it would be apparent that the waving lotion according to the present invention is superior in wave retention.

TEST 3

A human hair was practically waved by a usual permanent wave process, using each of the waving lotions obtained in Example 1 and Comparative Examples 1 and 2 and using a 6% aqueous solution of sodium bromate as the neutralizing lotion. The waving treatment was made for 10 persons for each waving lotion. The waved hairs were estimated with respect to the state of the treated hair (gloss, softness and wetting) and degree of foul smell (foul smell in the treatment with the waving lotion and foul smell after the completion of the permanent wave treatment).

The estimation was made in 5 ranks, and the average value of 10 data was shown as the result. With respect to the state of the hair, the larger the value, the better the state of the hair. With respect to the foul smell, the larger the value, the smaller the foul smell owing to mercaptan.

The results are shown in Table 4.

TABLE 4

| | State of hair | | | Weakness of foul smell | |
|---|---|---|---|---|---|
| | Gloss | Softness | Wetting | During treatment with waving lotion | After permanent waving treatment |
| Example 1 | 3.8 | 4.0 | 4.1 | 3.2 | 4.0 |
| Com. Ex. 1 | 3.6 | 3.6 | 3.4 | 1.9 | 2.8 |
| Com. Ex. 2 | 3.0 | 3.2 | 3.0 | 2.0 | 2.8 |

As apparent from Table 4, the waving lotion of Example 1 gave a remarkably reduced foul smell and moreover provided the hair with permanent wave in a better state, as compared with the waving lotions of Comparative Examples 1 and 2 using ammonium thioglycolate as the reducing agent.

TEST 4

A part of each hair wave-treated in Test 3 was cut and subjected to an amino acid analysis to determine cysteic acid in the hair.

The production of cysteic acid has relation to damage of the hair. The larger the cysteic acid content in the hair, the larger the damage of the hair caused by the wave treatment.

The results of the measurement of cysteic acid (average value of 10 persons' hairs) are shown in Table 5.

TABLE 5

| | Cysteic acid in the hair ($\mu$ mol/g) |
|---|---|
| Example 1 | 32 |
| Com. Ex. 1 | 36 |
| Com. Ex. 2 | 48 |

It would be apparent from Table 5 that the damage of the hair caused by the waving lotion of Example 1 is smaller than the waving lotion of Comparative Example 2 containing ammonium thioglycolate as the reducing agent and adjusted to pH 9.2, because of low cysteic acid content in the treated hair.

In case of the waving lotion of Comparative Example 1, the cysteic acid content is low and the damage of the hair owing to the wave treatment is small, but it is apparent that the waving lotion of Com. Ex. 2 cannot be put to practical use, because the lotion is adjusted to pH 6.8 and cannot sufficiently exhibit the reducing action of ammonium thioglycolate, thus resulting in poor wave-imparting effect and wave retention as shown in Tables 2 and 3.

EXAMPLE 2

A permanent waving lotion was prepared in the same manner as in Example 1 except that casein peptide was additionally used in an amount of 2% (concentration of effective ingredient, hereinafter the same). The pH of the waving lotion was 6.8.

The casein peptide used is a product of Seiwa Kasei Co., Ltd. sold under the trade mark "Promois Milk", and corresponds to a peptide of the formula (II) wherein n is about 5 (average value, hereinafter n showing an average value).

EXAMPLE 3

A permanent waving lotion was prepared in the same manner as in Example 1 except that potassium salt of collagen peptide acylated with coconut oil fatty acid was additionally used in an amount of 1%. The pH of the prepared waving lotion was 6.8. The used potassium salt of coconut oil fatty acid-acylated collagen peptide is a product of Seiwa Kasei Co., Ltd. sold under the trade mark "Promois ECP", and corresponds to an acylated peptide of the formula (III) wherein n is about 5.

EXAMPLE 4

A permanent waving lotion was prepared in the same manner as in Example 1 except that a quaternary ammonium derivative of keratin peptide, namely N-(trimethylammonio-2-hydroxypropyl)keratin peptide, was additionally used in an amount of 1%. The pH of the waving lotion was 6.8. The used quaternary ammonium derivative is a product of Seiwa Kasei Co., Ltd. sold under the trade mark "Promois WK-HQ", and corresponds to a quaternary ammonium derivative of peptide represented by the formula (IV) wherein n is about 10.

EXAMPLE 5

A permanent waving lotion was prepared in the same manner as in Example 1 except that ethyl ester of silk peptide was additionally used in an amount of 0.5%. The pH of the waving lotion was 6.8. The used silk peptide ethyl ester is a product of Seiwa Kasei Co., Ltd. sold under the trade mark "Promois Silk A", and corresponds to a peptide ester of the formula (V) wherein n is about 3.

EXAMPLE 6

A permanent waving lotion was prepared in the same manner as in Example 1 except that the same quaternary ammonium derivative of keratin peptide as used in Example 4 was additionally used in an amount of 2% and the pH was adjusted to 9.2 with aqueous ammonia.

The compositions of the permanent waving lotions prepared in Examples 2 to 6 are shown in Table 6.

TABLE 6

| Ingredients (part) | Ex. 2 | Ex. 3 | Ex. 4 | Ex. 5 | Ex. 6 |
|---|---|---|---|---|---|
| 2-Trimethylammonio-ethanethiol chloride | 6.0 | 6.0 | 6.0 | 6.0 | 6.0 |
| Casein peptide | 2.0 | — | — | — | — |
| Potassium salt of coconut oil fatty acid-acylated collagen peptide | — | 1.0 | — | — | — |
| Quaternary ammonium derivative of keratin peptide | — | — | 1.0 | — | 2.0 |
| Silk peptide ethyl ester | — | — | — | 0.5 | — |
| Ammonium bicarbonate | 2.5 | 2.5 | 2.5 | 2.5 | — |
| Monoethanolamine | — | — | — | — | 1.0 |
| Polyoxyethylene nonylphenyl ether | 0.2 | 0.2 | 0.2 | 0.2 | 0.2 |
| EDTA | 0.1 | 0.1 | 0.1 | 0.1 | 0.1 |
| Aqueous ammonia (28%) | *1 | *1 | *1 | *1 | *2 |
| Purified water | residue | residue | residue | residue | residue |
| Total | 100 | 100 | 100 | 100 | 100 |

(Notes)
*1 Aqueous ammonia was used in an amount to adjust to pH 6.8.
*2 Aqueous ammonia was used in an amount to adjust to pH 9.2.

The permanent waving lotions prepared in Examples 2 to 6 were tested according to Tests 1 to 4 with respect to wave-imparting effect (change in diameter of curl resulting from increase in the number of washings after imparting a wave to human hair), state of the wave-treated hair (luster, softness and wetting), smell (weakness of smell in use of the lotion and smell after permanent wave treatment), and damage of the hair owing to the wave treatment (cysteic acid content in the hair).

The results are shown in Table 7.

TABLE 7

| | Diameter of curl (mm) | | | Curl retention (%) | | | State of hair | | | Weakness of foul smell | | Cysteic acid in the hair ($\mu$ mol/g) |
|---|---|---|---|---|---|---|---|---|---|---|---|---|
| | Number of washings | | | After 1 day | After 5 days | After 10 days | Gloss | Softness | Wetting | During treatment with waving lotion | After permanent waving treatment | |
| | 0 | 3 | 5 | | | | | | | | | |
| Ex. 2 | 23.9 | 40.8 | 44.3 | 87 | 85 | 82 | 4.2 | 4.5 | 4.6 | 3.3 | 4.1 | 23 |
| Ex. 3 | 23.7 | 40.7 | 44.1 | 88 | 85 | 82 | 4.1 | 4.3 | 4.4 | 3.2 | 4.0 | 26 |
| Ex. 4 | 23.6 | 40.8 | 44.2 | 87 | 84 | 81 | 4.1 | 4.4 | 4.4 | 3.2 | 4.0 | 25 |
| Ex. 5 | 23.6 | 40.6 | 44.1 | 88 | 85 | 82 | 4.0 | 4.2 | 4.3 | 3.2 | 4.0 | 27 |
| Ex. 6 | 22.3 | 36.2 | 40.8 | 93 | 89 | 86 | 3.8 | 3.8 | 3.7 | 3.2 | 4.0 | 34 |

As apparent from Table 7, the cysteic acid content of the hairs treated with the permanent waving lotions of Examples 2 to 5 is lower than that of the hair treated with the waving lotion of Example 1 shown in Table 5. It would be apparent from these results that the damage of the hair is remarkably decreased by the addition of peptide or the derivative thereof. Also, the values indicating the state of the treated hair are larger than the case of Example 1 shown in Table 4, and these results show that the addition of peptide or its derivative improves the state of the hair. Other results, namely the diameter of curl, curl retention and weakness of foul smell, are on the same levels as in the case of Example 1, and it would be understood that the addition of peptide or its derivative does not substantially exert a bad influence on these characteristics.

From these results, it would be understood that, as compared with the permanent waving lotion of Comparative Example 2 containing ammonium thioglycolate and adjusted to pH 9.2, namely a conventional permanent waving lotion, the waving lotions of Examples 2 to 5 provide hairs with wave in a good state with a decreased damage and a decreased foul smell, and also the wave-imparting effect and wave retention are rather superior than the conventional waving lotion.

As shown in Example 6, when the permanent waving lotion according to the present invention is adjusted to an alkaline pH region, e.g. pH 9.2, and is incorporated with peptide or its derivative in order to prevent the damage of the hair, the wave-imparting effect is enhanced. The wave-imparting effect and wave retention of the waving lotion of Example 6 are extremely superior to the conventional waving lotion containing a thioglycolic acid reducing agent.

In addition to the ingredients used in the Examples, other ingredients can be used in the Examples as set forth in the specification to obtain substantially the same results.

What we claim is:

1. A permanent waving composition comprising 0.5 to 10% by weight of a quaternary ammoniomercaptan or its salt of the formula (1):

$$R^2-\overset{R^1}{\underset{R^3}{N^\oplus}}-A-SH \cdot X^\ominus \qquad (1)$$

wherein $R^1$, $R^2$ and $R^3$ are the same or different and each is an alkyl group having 1 to 3 carbon atoms or a hydroxyalkyl group having 1 to 3 carbon atoms, A is ethylene, group, and X is Cl, Br, I, $NO_3$, $\frac{1}{2}SO_4$, OH or $R^4OSO_3$ in which $R^4$ is an alkyl group having 1 to 3 carbon atoms.

2. The composition of claim 1, further comprising a peptide or a derivative thereof selected from the group consisting of acylated peptides, quaternary ammonium derivatives of peptides, and esters of peptides.

3. The composition of claim 1, wherein the composition is adjusted to a neutral or acidic pH region.

4. The composition of claim 1, wherein the composition is adjusted to an alkaline pH region.

* * * * *